(12) United States Patent
Kempe et al.

(10) Patent No.: US 9,348,127 B2
(45) Date of Patent: May 24, 2016

(54) METHODS AND APPARATUSES FOR STRUCTURED ILLUMINATION MICROSCOPY

(75) Inventors: Michael Kempe, Jena (DE); Gerhard Krampert, Jena (DE); Ingo Kleppe, Jena (DE); Ralf Wolleschensky, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 1165 days.

(21) Appl. No.: 13/121,466

(22) PCT Filed: Sep. 22, 2009

(86) PCT No.: PCT/EP2009/006818
§ 371 (c)(1),
(2), (4) Date: Mar. 29, 2011

(87) PCT Pub. No.: WO2010/037487
PCT Pub. Date: Apr. 8, 2010

(65) Prior Publication Data
US 2011/0182529 A1   Jul. 28, 2011

(30) Foreign Application Priority Data
Sep. 30, 2008   (DE) .......................... 10 2008 049 878

(51) Int. Cl.
*G06K 9/40*   (2006.01)
*G02B 21/00*   (2006.01)
(Continued)

(52) U.S. Cl.
CPC ........ *G02B 21/0032* (2013.01); *G01N 21/6458* (2013.01); *G02B 21/0076* (2013.01); *G02B 21/367* (2013.01); *G02B 27/58* (2013.01); *G02B 21/008* (2013.01); *G02B 21/0072* (2013.01)

(58) Field of Classification Search
None
See application file for complete search history.

(56) References Cited

U.S. PATENT DOCUMENTS 5,671,085 A   9/1997   Gustafsson
7,612,884 B2   11/2009   Wolleschensky et al.
(Continued)

FOREIGN PATENT DOCUMENTS

DE   199 08 883   9/2000
DE   101 55 002   5/2003
(Continued)

OTHER PUBLICATIONS

Wilson et al, "Method of obtaining optical sectioning by using structured light in a conventional microscope" Optics Letters 1997.*
(Continued)

*Primary Examiner* — Mark Roz
(74) *Attorney, Agent, or Firm* — Frommer Lawrence & Haug LLP

(57) ABSTRACT

In structured illumination microscopy, the multiple recording of images with different phase positions of the structuring requires a high stability in the optical arrangement and sample throughout the entire measuring process. Also, the structuring must be projected into the sample in a highly homogeneous manner. The current invention optimizes recording of individual images in order to achieve the best possible resolution in the result image even in problematic samples. An optimization of this kind can be carried out in different ways, for example, by determining an optimal adjustment for at least one illumination parameter or recording parameter or by pulsed illumination such that an excitation from a triplet state of the fluorescent dye to a higher triplet state is reduced, or by illuminating the sample with depletion light for depopulating a triplet state of the fluorescent dye, which reduces bleaching.

14 Claims, 7 Drawing Sheets

(51) Int. Cl.
*G01N 21/64* (2006.01)
*G02B 21/36* (2006.01)
*G02B 27/58* (2006.01)

(56) References Cited

U.S. PATENT DOCUMENTS

| | | | |
|---|---|---|---|
| 2003/0132394 A1* | 7/2003 | Wolleschensky et al. | 250/458.1 |
| 2004/0053354 A1* | 3/2004 | Ikawa et al. | 435/40.5 |
| 2006/0152791 A1 | 7/2006 | Wolleschensky et al. | |

FOREIGN PATENT DOCUMENTS

| | | |
|---|---|---|
| DE | 19853407 | 9/2003 |
| DE | 10 2006 011 176 | 9/2007 |
| DE | 10 2007 047 466 | 4/2009 |
| DE | 10 2007 047 468 | 4/2009 |
| EP | 1248132 | 10/2002 |
| EP | 1 617 259 | 1/2006 |
| EP | 1131664 | 9/2011 |
| JP | 2002-530715 | 9/2002 |
| JP | 2002-323660 | 11/2002 |
| JP | 2006-510886 | 3/2006 |
| JP | 2008-096778 | 4/2008 |

OTHER PUBLICATIONS

Notification of Reasons for Rejection for JP Application No. 2011-528231 dated Aug. 20, 2013.
Klaus-Peter Proll et al., "Application of a liquid-crystal spatial light modulator for brightness adaptation in a microscopic topometry", Applied Optics, vol. 39, No. 34, Dec. 1, 2000, pp. 6430-6435, XP-002560164.
Notification of Transmittal of Translation of International Preliminary Report on Patentability dated Apr. 14, 2011; The International Bureau of WIPO, Switerzland.
Christian Ringemann et al., "Enhancing Fluorescence Brightness: Effect of Reverse Intersystem Crossing Studied by Fluorescence Fluctuation Spectroscopy", ChemPhysChem 9, 612-624 (2008).
Mondal et al., "Image Reconstruction for Multiphoton Fluorescence Microscopy" Applied Physics 92, 103902 (2008).
Sauer et al., "Molecular Optical Switches and Waveguides", New Concepts for Tiny Photonic Devices, Photonics West 2008, Talk 6862-20.
Vogelsang et al. "A Reducing and Oxidizing System Minimizes Photobleaching and Blinking of Fluorescent Dyes", Supporting Information, 2008; pp. 1-5.

* cited by examiner

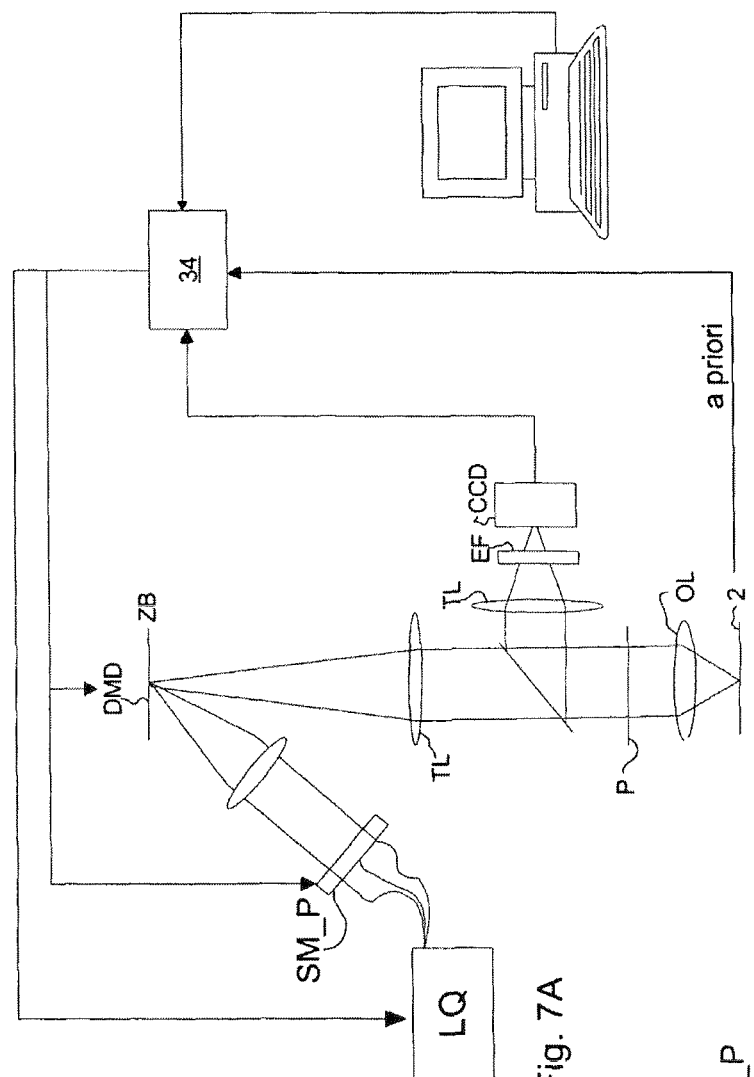

METHODS AND APPARATUSES FOR STRUCTURED ILLUMINATION MICROSCOPY

The present application claims priority from PCT Patent Application No. PCT/EP2009/006818 filed on Sep. 22, 2009, which claims priority from German Patent Application No. DE 10 2008 049 878.5 filed on Sep. 30, 2008, the disclosure of which is incorporated herein by reference in its entirety.

BACKGROUND OF THE INVENTION

1. Field of the Invention

The invention is directed to methods and devices for high-resolution microscopic imaging of a sample labeled with a fluorescent dye, wherein the sample is illuminated sequentially in a plurality of phases by structured, pulsed excitation light, and the fluorescent light emitted by the sample is recorded for each phase in a respective structured individual image so that a result image with enhanced resolution can be reconstructed from the individual images.

2. Description of Related Art

Due to the fact that the light received from the sample is diffracted in the microscope objective, the resolving power of microscopes depends upon the aperture of the objective and the wavelength of the light. Since the usable wavelength range of visible light is finite, the resolving power of a microscope is fundamentally limited (Abbe, 1873). As it relates to the spatial frequencies of the sample which are to be imaged, this means that the support of the optical transfer function (OTF) of the microscope is limited in frequency space to a finite region around the coordinate origin. Consequently, the microscope can only image those spatial frequencies lying within the center interval in which the support does not vanish.

By means of a structured illumination of the sample (structured illumination microscopy (SIM)), the resolving power can be improved, laterally and axially, approximately by a factor of two when the excitation intensity of the illumination and the emission intensity of the sample are in a linear relationship with one another. SIM is disclosed in U.S. Pat. No. 5,671,085, for example. It is based on the generation of a spatial light structure on the sample to be analyzed, for example, by means of a sinusoidal interference of the illumination light behind an optical grating. Due to the convolution of the excitation structure with the point spread function of the microscope objective in the spatial domain, a region of spatial frequencies of the sample structure lying outside the support of the OTF in the frequency domain is shifted to the center support interval, where they overlap the original spatial frequency intensities in that region. The light structure is generated sequentially in a plurality of different phase positions, and an individual image is recorded in each phase position. With the aid of an appropriate equation system, a consistent result image can be reconstructed from the individual images containing the superimpositions of the shifted spatial frequencies and original spatial frequencies, which result image contains the original spatial frequencies of the support interval as well as the original, higher spatial frequencies that have been shifted into the support interval in the meantime by the structured illumination. Therefore, the result image has a higher resolution than a conventional single recording with uniform illumination. However, taking multiple images with different phase positions and orientation of the structuring requires a highly stable optical arrangement and sample throughout the entire measuring process. Further, the required multiple recording reduces the effective frame rate. Also, the structuring must be projected into the sample in a highly homogeneous manner (constant frequency and phase in the structuring).

A considerable improvement in resolving power can be achieved by exciting the sample (by illumination or in some other manner) in such a way that there exists a nonlinear relationship between the excitation intensity and the light intensity emitted by the sample (saturated pattern excitation microscopy (SPEM)). SPEM is disclosed, for example, in DE 199 08 883 A1, the disclosure of which is hereby incorporated in its entirety. In fluorescence microscopy, a nonlinear excitation is achieved, for example, by a high illumination intensity leading to a partial saturation of the excitation of the fluorescent dye in the area of the illumination structure. In this way, spatial frequencies of object structures even higher than those in SIM are shifted into the OTF support interval. By taking the nonlinear interaction into account in the equation system to be solved, these higher frequencies can also be reconstructed. Compared to SIM, however, smaller phase steps and, therefore, even more individual images are required in SPEM. The nonlinear sample interaction encumbers the sample and sample dyes by bleaching. In addition, the nonlinearity depends not only on the illumination conditions but also on the local environmental conditions in the sample. As a result, distinctly different nonlinearities may be achieved at different locations in the sample, which makes reconstruction of the result image more difficult. In some cases, the environmental conditions in the sample can be so unfavorable for a nonlinear interaction that the use of SPEM is impossible.

In SIM and SPEM, the resolution which can be achieved by reconstruction is fundamentally limited by the signal-to-noise ratio (SNR) in the recording of individual images.

SUMMARY OF THE INVENTION

It is the object of the invention to improve methods and devices of the type mentioned above in such a way that the highest possible resolutions can be achieved.

This object is met by methods and devices having the features indicated in the independent claims.

Advantageous embodiments are indicated in the dependent claims.

The core of the invention consists in the optimization of the raw data contained in the individual images in order to achieve the best possible resolution in the result image even in problematic samples. An optimization of this kind can be carried out in different ways according to the invention.

According to the invention, it was recognized that the resolution in SIM and SPEM is impaired by the following factors among others: The phase of the illumination light and fluorescent light is locally distorted by the optical system (e.g., in the form of aberrations) as well as by the optical sample characteristics, especially of thicker samples. Further, the modulation contrast of the structuring decreases as the depth of penetration into the sample increases due to scattering and aberrations resulting from local and global variations in the refractive index, referred to as mismatch. This effect also depends on the structuring frequency which is used. Lower-frequency modulations can be projected at a greater depth into the sample but, on the other hand, also lead to a lower resolution in the result image. Accordingly, depending on the sample being analyzed, a different combination of structuring parameters (such as the relative angle and the relative intensity of the beam components which bring about the structuring through interference) is required to obtain an optimal result image. In the case of dye molecules which have already been excited, when further excited into a higher energy state there is a high probability of irreversible bleaching, which results in a reduced signal-to-noise ratio and, accordingly, in a reduced resolution in the reconstruction. In addition, a low image contrast results when the electric or electronic gain of the recorded fluorescent light is too low (underexposure) or too high (overexposure), which impairs or prevents reconstruction.

Therefore, according to the invention, an optimal adjustment is determined for at least one parameter of the illumination and/or at least one parameter of the recording, particularly for at least one of the quantities including "wavelength of the illumination", "pulse sequence of the illumination", "wavelength range of the recording", "exposure time of the recording", and "gain of the recording". Within the meaning of the invention, an adjustment is a one-dimensional or two-dimensional value. An adjustment is optimal within the meaning of the invention when a specifiable target value reaches a maximum or reaches at least a specifiable threshold value in this adjustment. Target values may include recording time, signal-to-noise ratio, or the dynamic range of the detected fluorescence signal. The fluorescence yield and, therefore, also the signal-to-noise ratio can be improved economically and bleaching of the sample can be prevented by the optimization according to the invention. As a result, the resolution depending on the signal-to-noise ratio is improved. In addition, the optimization can also promote system safety because damage to the camera used for recording caused by overexposure can be prevented by entering the camera specifications in the optimization as boundary conditions. The parameter "pulse sequence" means the pulse duration and/or pulse repetition frequency. An adjustable electron multiplication factor (electron multiplication gain, or EM gain) can be optimized as the "gain of the recording" parameter.

The optimal adjustment can be determined and used in a subsequent recording of individual images in a fully automated manner. Alternatively, it can be determined in a semi-automated manner by a user command and used as a preset for an elective adjustment of the parameter by a user. It is also conceivable for the optimized adjustment to be presented to the user merely for confirmation, in which case the user may opt to interrupt the measurement, for example. Of course, optimal adjustments can be determined in an optimization pass for a plurality of parameters.

The relevant quantities for optimization can be divided into information that is known or that can be determined a priori and into parameters that can only be obtained by feedback based on recorded images. Parameters which are known a priori or which can at least be determined a priori are, for example, dye characteristics (bleach rate, switching cycles for SPEM excitation, and excitation spectra and emission spectra of all of the bands), characteristics of the embedding medium of the sample (refractive index, autofluorescence spectra) and the desired depth of penetration. Accordingly, the optimal adjustment of the parameter to be optimized or of a plurality of parameters to be optimized is preferably determined by feedback based on the individual images, based on additional intermediate images, or based on a signal of a point detector to which a fraction of the fluorescent light is coupled out, and by varying the parameter. Accordingly, instead of a rough calculation from a refractive index mismatch of the sample which is known a priori, the pulse repetition frequency, for example, can be optimized with high accuracy through an evaluation of individual images by recording and analyzing a plurality of individual images with different pulse repetition frequencies. By intermediate images is meant within the meaning of the invention all images which are not used in a subsequent reconstruction. In particular, the individual images can be composed of a plurality of intermediate images by integration if their frame rate is correspondingly high. For purposes of optimizing a plurality of parameters, the variation must be carried out correspondingly in multiple dimensions.

In particularly preferred embodiment forms, the variation of the parameter is carried out at a substantially constant average output of the excitation light because an increase in the signal (i.e., an improved signal-to-noise ratio) can only take place through reduced bleaching. The constant average output of the excitation light used is preferably that which is also used in the recording of the individual images to be used for the reconstruction.

As an alternative to variation and empirical feedback, a simulation of illumination, response of the sample, and recording can be carried out to determine the optimal adjustment of the parameter, preferably using the known a-priori information. In this connection, a variation of the parameter to be optimized is also advisably carried out in order to determine the optimal adjustment. This does not stress the sample because bleaching is entirely prevented. Nevertheless, the optimal adjustment of the parameter to be optimized can be optimized with high accuracy. The simulation is advantageous for protecting the sample particularly when a plurality of parameters are to be optimized.

Preferably, an adjustment is determined as optimal when a maximum signal-to-noise ratio or at least a predetermined signal-to-noise ratio results (at least in a variation) in an intermediate image, in an individual image, or in the result image by this adjustment. In this way, the resolution of the result image can be maximized automatically or influenced by the user. Owing to the dependency of the resolving power of the SIM and SPEM methods, the highest possible signal-to-noise ratio in the individual images is essential for a reconstruction with as few artifacts as possible.

Beyond this, in advantageous embodiment forms, a predetermined weighting of additional optimization goals is taken into account in addition to a weighting for the signal-to-noise ratio when determining the optimal adjustment. In this way, the user can set priorities for the optimization. For example, the optimization can be implemented primarily with a view to a short recording time and only secondarily to a maximum signal-to-noise ratio. Another possible optimization goal that can be pursued either primarily or with a lower priority is to utilize the dynamic range of the recording camera to the fullest possible extent.

In a first alternative form of feedback, the recording of the fluorescent light for the optimization is carried out as an alternative to or in addition to the recording of the individual images in intermediate images, advantageously with a frame rate which corresponds approximately to the frame rate in the recording of the individual images so that the fluorescent light is integrated over many pulse sequence cycles.

In a second alternative form of feedback, the recording of the fluorescent light in intermediate images is advantageously carried out with a significantly higher frame rate than when recording the individual images. The high frame rate allows a more sensitive analysis of the excitation behavior and emission behavior of the sample. Intermediate images or even individual images with longer exposure times can be calculated by summing the intermediate images. In so doing, intermediate images with different exposure times can advisably be normalized by means of a computer.

In connection with the high-frequency recording of intermediate images by means of a locally variable imaging unit, it is advantageous to vary the pulse sequence locally, particularly pixel by pixel. For example, spatial light modulators (SLM) such as digital micro-mirror devices (DMD), liquid crystal displays (LCD), or LCOS (liquid crystal on silicon) can be used as imaging units. An imaging unit is advisably arranged in an intermediate image plane of the illumination beam path. In addition to a global variation of the pulse sequence in the entire illumination field, local variation can serve not only to adapt the pulse sequence to different local conditions on the sample (for example, regions which are dyed with different fluorescent dyes) within the framework of the fed-back optimization, but can also expand the dynamics of the individual images. The dynamics can be expanded globally or locally up to the point of full driving of the recording camera or even beyond this. The expansion of dynamics is achieved particularly by feedback with mean values of whole intermediate images or with regions or pixels of intermediate images or also with individual images. For example, when recording intermediate images which are summed to form an individual image, the illumination and/or the image recording (exposure) can be terminated in a region or in a pixel when a sufficient signal-to-noise ratio is achieved with minimal bleaching or when a predetermined intensity threshold is achieved, while the illumination and/or the image recording proceeds on the rest of the sample. The illumination variations and exposure variations resulting in this way are advisably stored with the recorded image data. Individual images during whose recording the pulse sequence was varied are expanded with respect to their dynamic range prior to the reconstruction of the result image by correcting their intensity based on the stored variation information corresponding to the variation of the pulse sequence. The stored information about the expanded dynamics can also be used for an optimal reproduction taking into account the dynamics of the respective visualization medium. A global or local expansion of dynamics, particularly by means of a locally variable imaging unit, can also be carried out independently from the optimization.

An additional imaging unit can advantageously be dispensed with in that the variation of the pulse sequence and the structuring of the excitation light are both generated by means of the same imaging unit.

Since the processes according to the invention are of relatively long duration, a measurement abort criterion is advantageously checked during the recording and displayed during the measurement, and the recording is terminated or at least simplified when the measurement abort criterion is met. A simplification may consist, for example, in switching from a SPEM measurement exclusively to SIM measurement when it is determined on the basis of feedback with intermediate images or individual images that a sufficient degree of nonlinearity has not been achieved by excitation.

In an advantageous manner, as a measurement abort criterion, a check is made as to whether a modulation contrast falls below a predetermined contrast threshold or whether a movement distance of the sample exceeds a movement threshold. The modulation contrast can be determined continuously, for example, in all of the intermediate images and individual images. A movement of the sample can occur, for example, due to drift. A movement can be flagged, for example, by correlating between intermediate images or individual images. In so doing, the modulation frequency of the structured illumination must be filtered out of the images beforehand in order to obtain the desired change of phase position. Another possibility for identifying and analyzing movements of the sample consists in the simultaneous recording of images with differential interference contrast (DIG) in transmitted light. This is particularly advantageous when examining living cells.

Optimization according to the invention need not be carried out on regular samples, but may also be carried out in a particularly advantageous manner on test preparations, on the basis of which the optimal adjustment(s) can be obtained as a-priori information for the recording of images of regular samples. Test preparations which are particularly advantageous for structured illumination are homogeneous, optically thin (less than 100 nm thickness) multi-colored dye films with no refractive index mismatch with the immersion liquid of the objective (i.e., without interferences), and test samples with multi-colored beads between 200 nm and 500 nm in size. Good results for optimization of the modulation contrast and the phase consistency of the structuring can be obtained especially with dye films, while the bead test samples are advantageous for a calibration of the co-localization in a plurality of color channels.

According to the invention, it was also recognized that the sensitivity of dye molecules in the excited state can be reduced in that the illumination is carried out spatiotemporally with a pulse sequence such that an excitation from a triplet state (particularly the lowest triplet state) of the fluorescent dye to a higher triplet state is reduced. This minimizes excitation of molecules which are still excited and accordingly prevents bleaching. An image recording technique of this kind was published in DE 10 2006 011 176 A1 for stimulated emission depletion (STED) microscopy. When the high peak intensities required for SPEM are achieved by pulsed laser, the pulse repetition frequency of the laser is reduced, according to the invention, for using the T-Rex technique in SPEM to the extent that the vast majority of excited dye molecules is already relaxed again in the singlet ground state until the next laser pulse. If the required peak intensities are achieved by structured line illumination (SLIM) according to DE 10 2007 047 468 A1, the disclosure of which is hereby incorporated in its entirety, this line must be moved over the sample by scanning fast enough that the dwell time of the line on a point is so short that a dye molecule is excited on the average only once per pass of the line. If the speed of the scanning movement is not sufficient to do this, the fast scanning can be supplemented through an additional continuous on-and-off switching of the laser during the scan (blanking) as part of the pulse sequence in order to prevent further excitation of already excited dye molecules.

Preferably, a pulse sequence having a dead time of one or more microseconds between the pulses of excitation light is used. The optimal pulse sequence and, in the case of scanning line illumination, possibly the optimal scanning speed can be determined automatically or semi-automatically particularly by the methods according to the invention which are described above.

According to the invention, it was further recognized that bleaching can be prevented not only through pulsed excitation but also by additional illumination of the sample with depletion light for depopulating a triplet state (especially the lowest triplet state) of the fluorescent dye. Through active depopulation of triplet states by means of a suitable laser illumination in a second wavelength (Eggeling et al., ChemPhysChem 9, 612-624 (2008); Mondal, Appl. Phys. Lett. 92, 013902, 2008). For this purpose, for instance, a second light source is coupled into the beam path. This can be carried out simultaneous with excitation when the depletion light is separated from the fluorescence on the detection side.

The depletion light is advisably structured in the same way as the excitation light which protects the sample.

In an advantageous manner, depletion light with an energy density of one or more $MW/cm^2$ is used. Previously conducted experiments and simulations suggest that such high intensity values for the depopulating beam are required for an effective depletion. These intensities are preferably achieved by line illumination.

It was further recognized according to the invention that the accuracy of the reconstruction of the result image and, therefore, the achievable resolution can be improved by recording intermediate images on the basis of which an amount of bleaching of the fluorescent dye caused by the illumination can be determined, and in that the individual images are corrected computationally corresponding to the determined amount prior to the reconstruction of the result image. Taking the bleaching behavior into account allows a reconstruction with enhanced resolution even with difficult samples. Bleaching in structured illumination is, in fact, a problem which is spatially modulated by the sample and illumination. But it is precisely this that the invention can make use of for specific corrections. Bleaching can be factored in as another unknown in the equation system describing the overlapping of the spatial frequencies of the sample with the modulation frequency of the structured illumination. In order to solve the equation system, smaller and consequently more phase steps are needed.

The intermediate images are preferably recorded before the individual images, or one intermediate image is recorded between two individual images, respectively, wherein the sample is illuminated in a structured or uniform manner. Ideally, when all of the intermediate images are summed with equidistant phase steps (e.g., of 60° with five phase images per grating direction) between two recordings of individual images, a sum image without structuring should result. With correct phase steps (which can be verified on a bleaching-resistant test sample), any residual structuring at the structuring frequency arises from bleaching and can be corrected in the individual images for all of the subsequent images before reconstruction. Alternatively, an image without structuring can also be recorded at regular intervals during the recording of the individual images and the same correction process can be applied. For example, a recording can be made without a grating between two recordings with an altered phase position of the grating. In view of the fact that in good approximation, provided the samples are not too thick, bleaching is not dependent on the focus position, this method can also be applied when recording a z-stack, where the entire axial scanning area is typically scanned between two grating movements. All of the corrected individual images can be summed to check the bleaching correction. The correction is successful when there is a constant intensity in the sum image.

For each grating position and focus position, the intermediate images are preferably recorded at a higher frame rate than the individual images and the bleaching is determined pixel by pixel from a decrease in intensity of the fluorescent light. This can take place in direct combination with the local or global parameter optimization according to the invention. In this case, the images averaged over all of the images associated with a grating position and focus position after correction of the bleaching effect (taking into account all of the preceding recording steps) are correlated. It is also possible to correct the bleaching effect after determination directly during the subsequent recordings (intermediate images and/or individual images).

The computational correction of bleaching is preferably carried out in Fourier space with the corresponding amplitude.

According to the invention, it was further recognized that the accuracy of the reconstruction and, therefore, the achievable resolution, can also be improved in that an amount of an optical aberration of the individual images is determined based on at least one reference image and the individual images are computationally corrected corresponding to the determined amount prior to the reconstruction of the result image. In this case also, precisely those image characteristics resulting from the structuring can advantageously be used for correction.

The amount of aberration is preferably determined based on a distortion of the structuring pattern, particularly a deformation and/or spatial phase change. Field-dependent aberrations can be deduced from the distortion of the structuring pattern and used after evaluation of the grating structure to correct the entire image.

In an advantageous manner, a reference excitation light with a moderate structuring spatial frequency, preferably a structuring spatial frequency which is lower that during the recording of the individual images, is used for a recording of the reference image. Assuming that the nonlinearity in SPEM is the same at both low and high modulation frequencies, this prevents the set of problems associated with a small modulation depth at high spatial frequencies.

The structuring of the excitation light is preferably carried out by means of three diffraction orders, and the reference image is determined in that spatial frequencies just above a spatial frequency of an interference of all three diffraction orders are filtered. When diffraction orders of 0 and ±1) are used in the illumination for generating the structuring, a structuring at half of the spatial frequency (interference of diffraction orders of 0 and ±1) takes place in the image in addition to a structuring at the high spatial frequency (interference of the diffraction orders of ±1). After filtering all of the spatial frequencies just above the lower structuring frequency, a suitable image is available for correcting aberrations.

The fluorescence excitation for SPEM is preferably carried out in such a way that there is a nonlinear relationship between excitation intensity and fluorescence intensity. In particular, a photoswitchable fluorescent dye such as Dronpa can be used to achieve a nonlinearity, and a pH value and/or an oxygen concentration and/or a sample fixation can be optimized with respect to a switching contrast of the fluorescent light. For SPEM, the switching contrast is the decisive variable for the resolution that can be achieved. According to the invention, it was recognized that the pH value, the oxygen concentration, and the manner in which the sample is fixated are in turn decisive for the switching contrast. The amplitude of the higher orders of modulation generated by the nonlinearity can be determined from the reconstruction algorithm for the structured illumination. This is a measure of how optimally these parameters (pH value, fixation) were chosen. These parameters can now be optimized with respect to a maximum switching contrast through a series of sample preparations.

In spite of this optimization, the conditions for nonlinear interaction may vary at different locations of the sample. Therefore, in a first alternative embodiment, the illumination for recording the individual images is varied locally, particularly pixel by pixel, according to the invention. By means of such a spatial adaptation (or temporal adaptation for different individual images), the optimal nonlinearity can be achieved temporally continuously and spatially at all locations because the nonlinearity depends not only on the environmental conditions but also on the illumination conditions, namely, particularly the excitation intensity and the intensity of the activation laser.

In a second alternative embodiment, the structuring is carried out with a modulation frequency which is low enough that even multiples of this frequency still fall within a transmission range of an objective lens of the microscope. An amplitude of harmonics in the sample is then determined and used in a criterion for an optimal adjustment of a parameter, particularly for at least one of the variables including "wavelength of the illumination", "pulse sequence of the illumination", "wavelength range of the recording", "exposure time of the recording", and "gain of the recording." This procedure may be referred to as modulation zoom. Due to the fact that harmonics of the modulation frequency are generated in the sample by the nonlinear sample interaction and can also be transmitted by the objective, the amplitude of these harmonics in the image can advantageously be used as a measure for optimal SPEM conditions. Determining the harmonics amplitude by means of modulation zoom requires substantially fewer intermediate images compared with the acquisition of information by means of the reconstruction algorithm and accordingly reduces stressing of the sample.

On the other hand, determining the harmonics amplitude by means of the reconstruction algorithm has the advantage that there is no need to make changes to the modulation frequency at the microscope in the direction of very low frequencies; rather, only fixed modulation frequencies are needed. The optimization of the illumination parameters need not be carried out globally over the entire image, but can also be carried out locally. In case of spatially optimal activation (photoswitch) or excitation, the evaluation with the SPEM algorithm must be carried out in a plurality of regions of interest (ROI) of the sample and the illumination intensities in these ROIs must be adapted in a corresponding manner or, for the modulation zoom technique, the evaluation of the amplitudes of the harmonics must be carried out in a plurality of ROIs.

According to the invention, it was further recognized that, in SPEM, the signal-to-noise ratio and, therefore, the achievable resolution can be increased in that radicals which are contained in the sample and which can react chemically with the excited fluorescent dye are chemically removed from the environment of the fluorescent dye and/or of the sample. This makes it possible to influence the environmental dependence of the nonlinear effect and the variability thereof in such a way that SPEM is possible in inhomogeneous samples. The high spatial and temporal peak intensities in SPEM lead to increased bleaching of the dyes. This bleaching is chiefly caused by chemical reactions from the excited states (singlet and triplet states). Since all of the dye molecules in these excited states are especially sensitive to destructive chemical reactions with their environment, the bleaching can be reduced and, therefore, the signal-to-noise ratio improved by removing particularly reactive environmental molecules (radicals) from their environment through chemical processes.

For purposes of elimination, these radicals, for example, oxygen radicals, are advantageously reacted away enzymatically and are therefore removed from the sample. Corresponding reactions for other radicals are also described in chemical literature. A combination of radical-removing reactions for sample preparation was described under the name ROXS [Sauer et al., Photonics West 2008, Talk 6862-20].

In particularly preferred embodiment forms of the methods according to the invention, the sample is excited by structured line illumination. This makes it possible to use high excitation powers.

In so doing, an intensity of the line illumination is advantageously adjusted in such a way that a dynamic range of a recording camera is fully utilized and the intensity is stored line by line. A high dynamic range means a high signal-to-noise ratio and, therefore, a high resolution.

The fluorescent light is preferably detected confocally, particularly by means of a laser scanning microscope. In this way, out-of-focus light is efficiently discriminated and the signal-to-noise ratio is accordingly improved. By combining confocal detection with structured line illumination, background which may possibly be disruptive for the feedback is reduced already during image recording.

All of the methods according to the invention can be combined with one another.

BRIEF DESCRIPTION OF THE DRAWINGS

FIG. 7 shows a schematic view of another widefield microscope with fiber-optic structuring module and variation of local illumination.

DETAILED DESCRIPTION OF EMBODIMENTS

Figure 1:
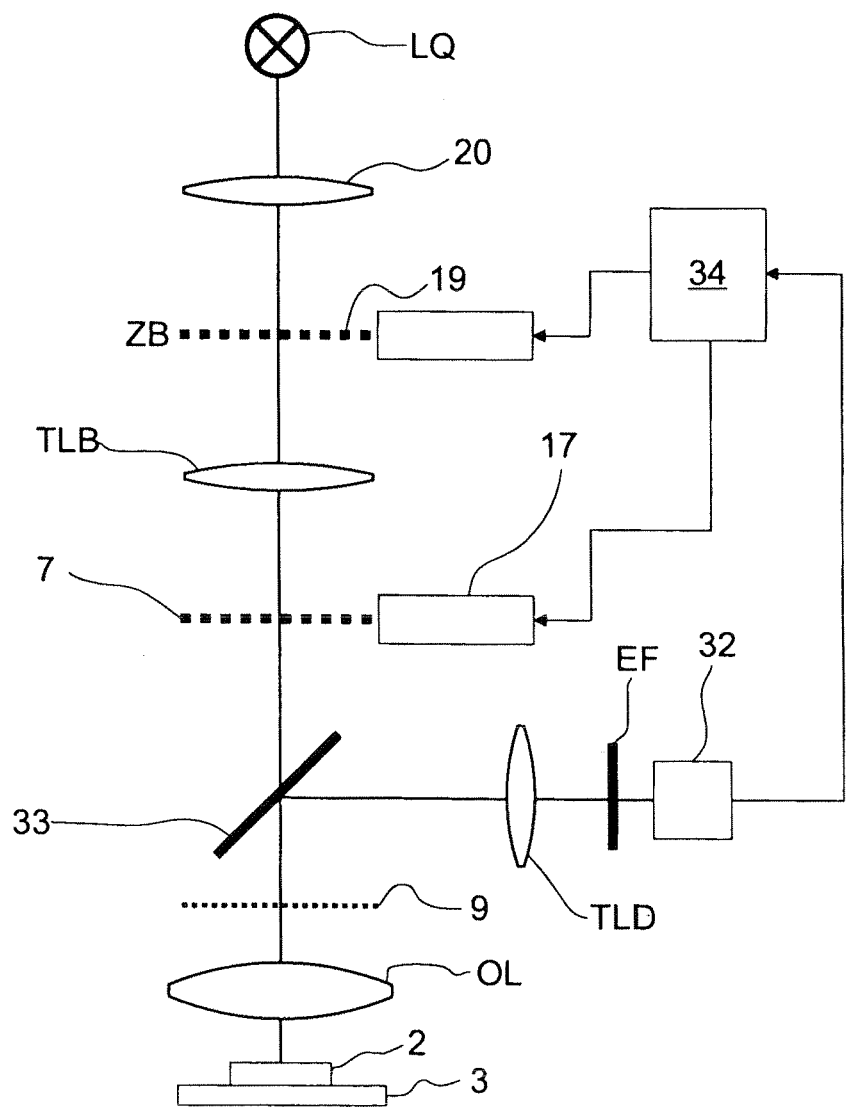
FIG. 1 shows a schematic view of a widefield microscope.

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Identical parts have identical reference numerals in all of the drawings.

FIG. 1 shows a schematic view of the beam path of an arrangement for widefield fluorescence microscopy serving by way of example, in which the SIM and SPEM methods which are improved by the invention can be used. The sample 2 is arranged on a positionable sample holder 3 in front of the microscope objective 5. A mask with phase structures according to DE 10 2007 047 466 A1, the disclosure of which is hereby incorporated in its entirety, is arranged as a structuring module 7 in the vicinity of the pupil 9 of the microscope objective OL or of a plane conjugate to the latter in order to generate a structured light distribution on or in the sample 2. The mask of the structuring module 7 can be moved by an actuator 17, which could be a stepper motor for rotating the mask, or a linear drive. A stepper motor can drive a round mask directly or indirectly by means of a gear unit or other mechanical unit. An imaging unit 19, for example, an LCD, as a temporal and spatial optical modulator lies in an intermediate image plane ZB which is generated by the tube lens TLB and which is conjugate to the sample plane. The light source LQ illuminates the element 19 and can be a laser, an LED, a high-pressure mercury lamp or a conventional incandescent lamp, for example. Optional collimating optics 27 can be provided in addition. The light source LQ can be monochromatic or can emit a plurality of wavelengths simultaneously or sequentially in time. In a preferred implementation of the invention, the phase mask of the structuring module 7 is located in, or in the vicinity of, the pupil 9 of the objective. For design reasons, the pupil in many microscope objectives is not directly accessible. However, in this case an intermediate imaging can be carried out by relay optics in a freely accessible intermediate image plane in whose vicinity the phase mask of the structuring module 7 can be arranged. Depending on the distance of the phase mask 7 from the pupil plane, the diameter of the individual diffraction orders increases as the distance from the pupil plane increases. By means of the imaging unit 19, the light emitted by the light source LQ can be divided temporally into a pulse sequence for fluorescence excitation on the one hand and two-dimensionally, pixel for pixel, transverse to the optical axis on the other hand. Further, a spatially resolving detector array 32, for example, a CCD, is provided behind a tube lens TLD as a camera for image recording. In the arrangement for fluorescence detection described herein, a main color splitter 33 for separating fluorescent light and excitation light and an emission filter EF are provided.

Figure 2:
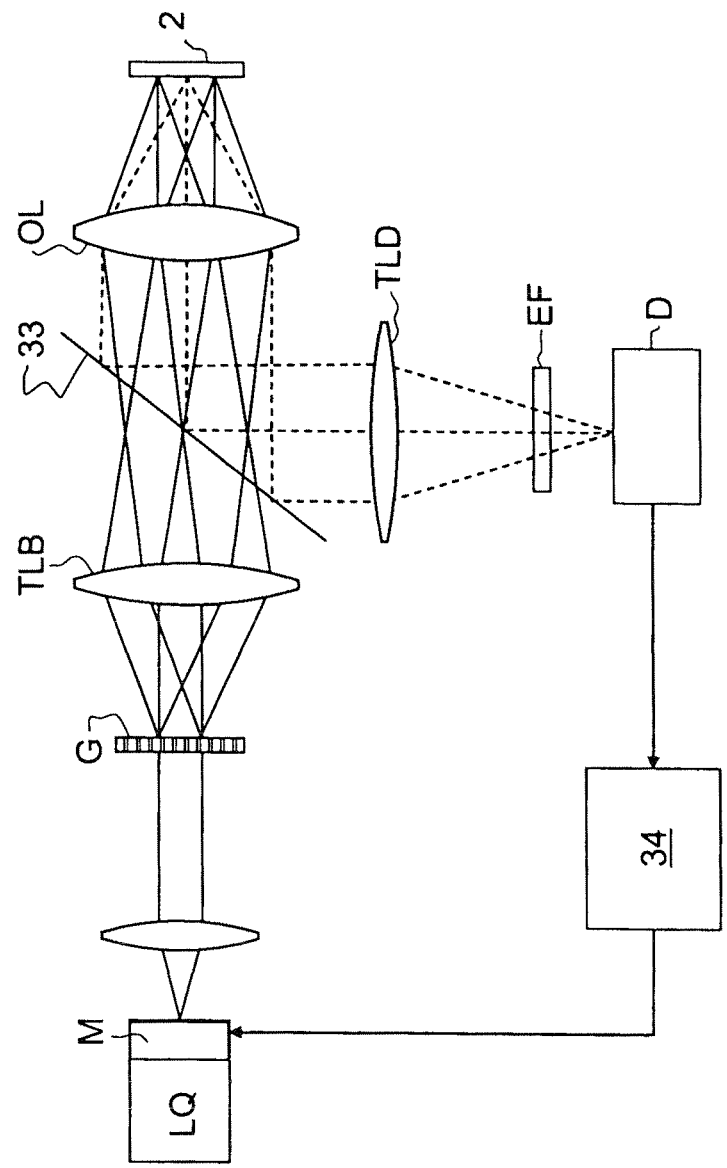
FIG. 2 shows a schematic view of a beam path of another widefield microscope.

FIG. 2 shows the beam paths in a widefield microscope in which, as a modification of the arrangement according to FIG. 1, the illumination structure is generated by a structuring module having a rigid grating G which is displaceable or rotatable in a plurality of different phase positions. The light source LQ is pulsed for fluorescence excitation or is outfitted with a fast optical modulator M, the pulse sequence in both cases being controlled by the control unit 34. The beam path is shown by way of example in the drawing and may be replaced by different beam paths to represent a widefield illumination and widefield detection as is well-known to the person skilled in the art, or a confocal beam path of a scanning microscope or of a microscope with parallel confocal illumination and detection as when using Nipkow disks.

Figure 3:
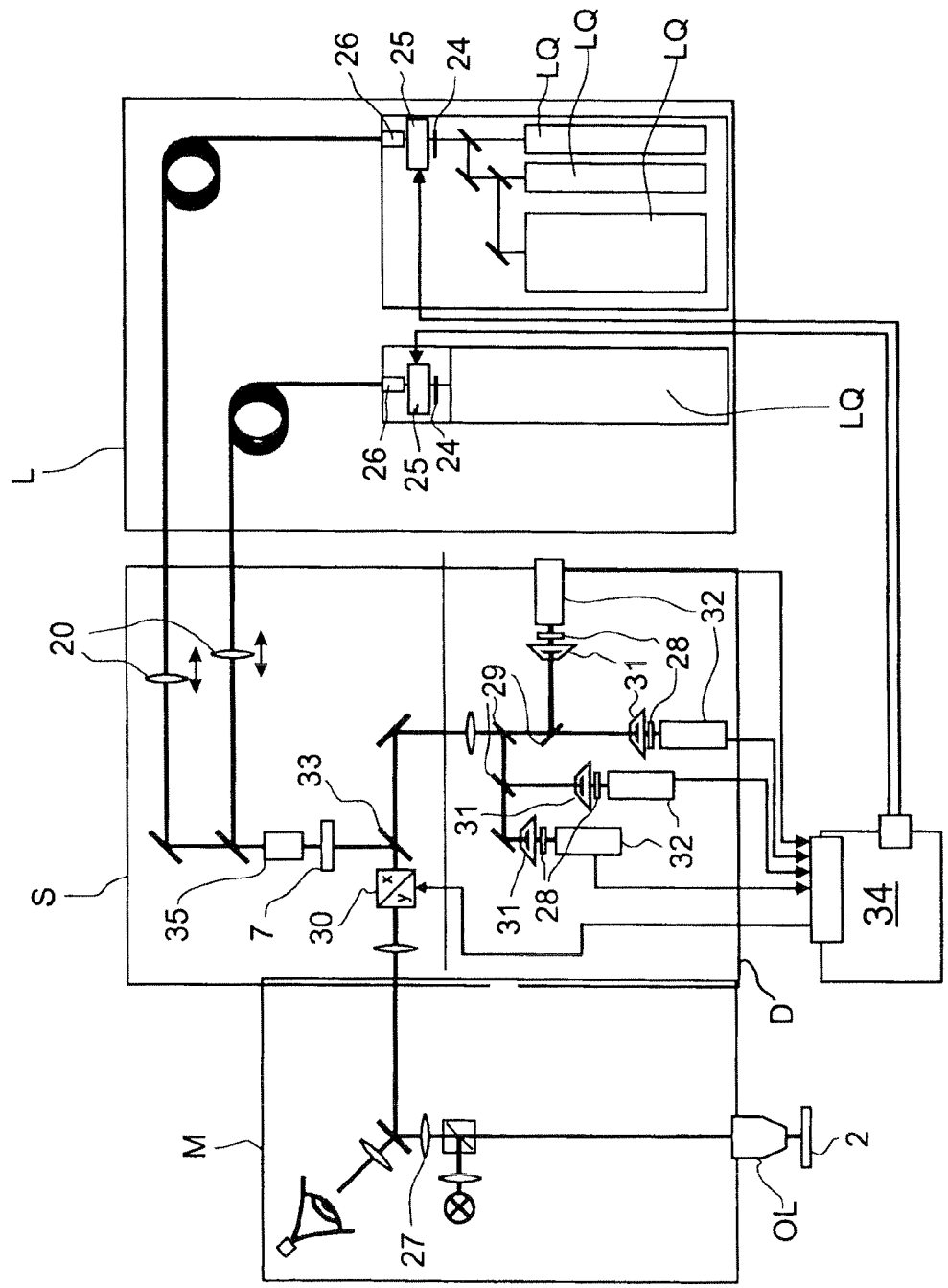
FIG. 3 shows a schematic view of a laser scanning microscope.

In a schematic view, FIG. 3 shows an arrangement by way of example in which the SIM and SPEM methods which are improved according to the invention can likewise be used for scanning fluorescence microscopy by means of a laser scanning microscope (LSM). The LSM is controlled by a control unit 34. The LSM is composed in a modular manner of an illumination module L with lasers as light sources LQ, a scanning module S, a detection module D, and the microscope unit M with microscope objective OL. The light of the laser light sources LQ can be influenced by the control unit 34 through light flaps 24 and attenuators 25 for purposes of a pulsed illumination before being fed via light-conducting fibers and coupling optics 20 into the scanning unit S and is combined after cylindrical optics 35 and a structuring module 7. The structuring module 7 can be constructed, for example, so as to be displaceable or rotatable as a grating or phase mask for a recording in a plurality of phase steps. The cylindrical optics are used for beam shaping for line illumination. Through the main beamsplitter 33 and the X-Y scanning unit 30 which has two galvanometric mirrors (not shown), the illumination light passes through the microscope objective OL to the sample 22, where it illuminates a line-shaped focal volume (not shown). Fluorescent light emitted by the sample passes through the microscope objective 21 via the scanning unit 30 through the main beamsplitter 30 into the detection module D. The main beamsplitter 30 can be constructed, for example, as a dichroic color splitter for fluorescence detection. The detection module D has a plurality of detection channels, each having a slit diaphragm 31, a filter 28, and a line-shaped (linear) detector array 32 with a plurality of detection elements. The detection channels are separated by color splitters 29. The confocal slit diaphragms 31 serve to discriminate sample light not originating from the focal volume. Therefore, the detector arrays 32 detect exclusively light from the focal volume. The confocally illuminated and recorded focal volume of the sample 22 can be moved over the sample 22 by means of the scanning unit 30 in order to record an image pixel by pixel by means of the detectors 32 serving as camera in that the galvanometric mirrors of the scanning unit 30 are rotated in a specific manner. Both the movement of the galvanometric mirrors as well as the switching of the illumination are controlled indirectly by the control unit 34 by means of the light flaps 24 or the attenuator 25. The data recording of the detector arrays 32 is likewise carried out by means of the peripheral interface 4.

In order to increase the fluorescence yield and the signal-to-noise ratio and to prevent bleaching, it is advisable to use a short, pulsed excitation in the range of a few nanoseconds, wherein there is a pause of a few microseconds between the excitation pulses. A reduction in the excitation from the lowest triplet state to higher triplet states can be achieved in this way. For this purpose, the camera for image recording integrates with conventional exposure times (i.e., over many pulse sequence cycles). The mean excitation power reduced by the low pulse repetition frequency and the short pulse duration is offset at least partially by an increased fluorescence yield. Possible light sources include pulsed lasers (mode-coupled or Q-switched lasers), possibly with a fast optical modulator (pulse picker) for reducing the pulse repetition frequency, for example, an acousto-optical modulator (AOM), or fast laser diodes or light emitting diodes (LED) which are modulated directly by the drive current.

Figure 4:
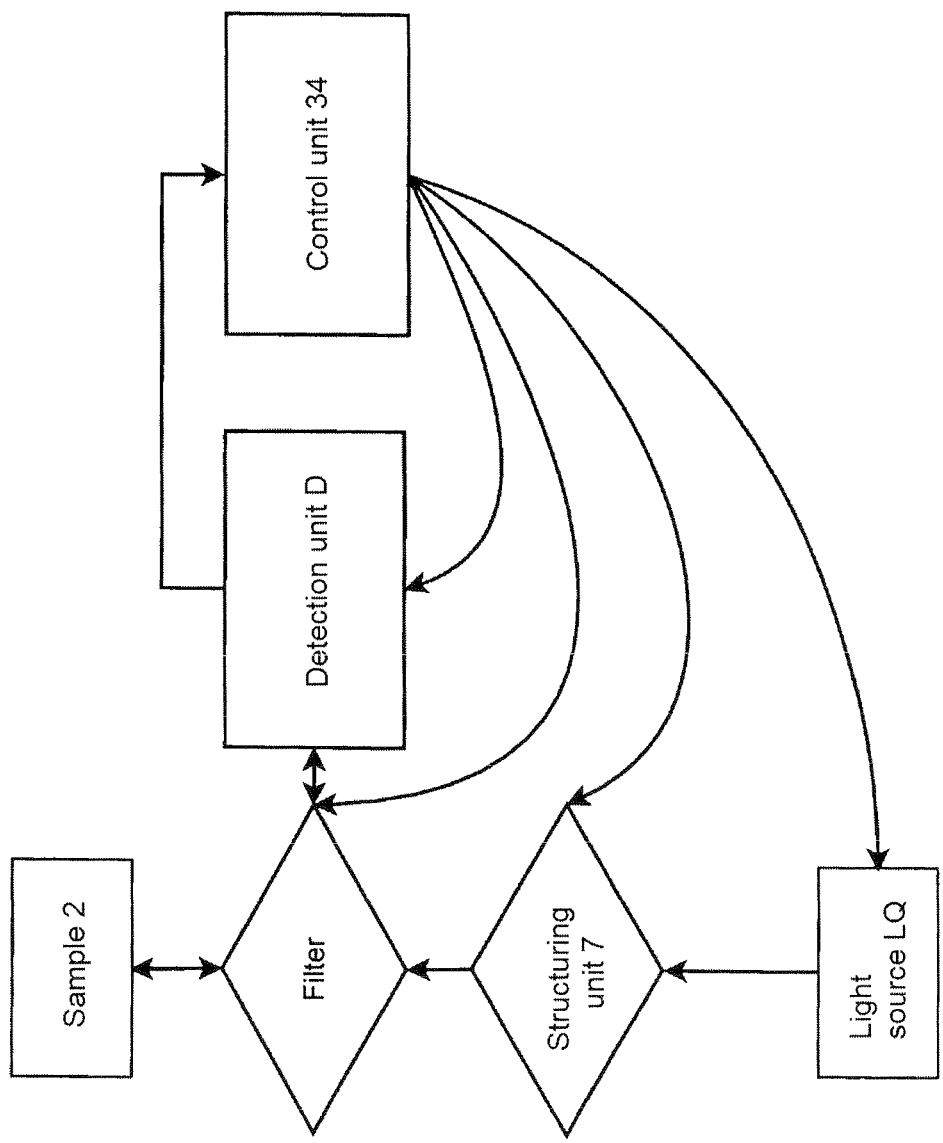
FIG. 4 shows a pseudo-flowchart of the basic optimization method based on feedback and readjustment.
Figure 5:
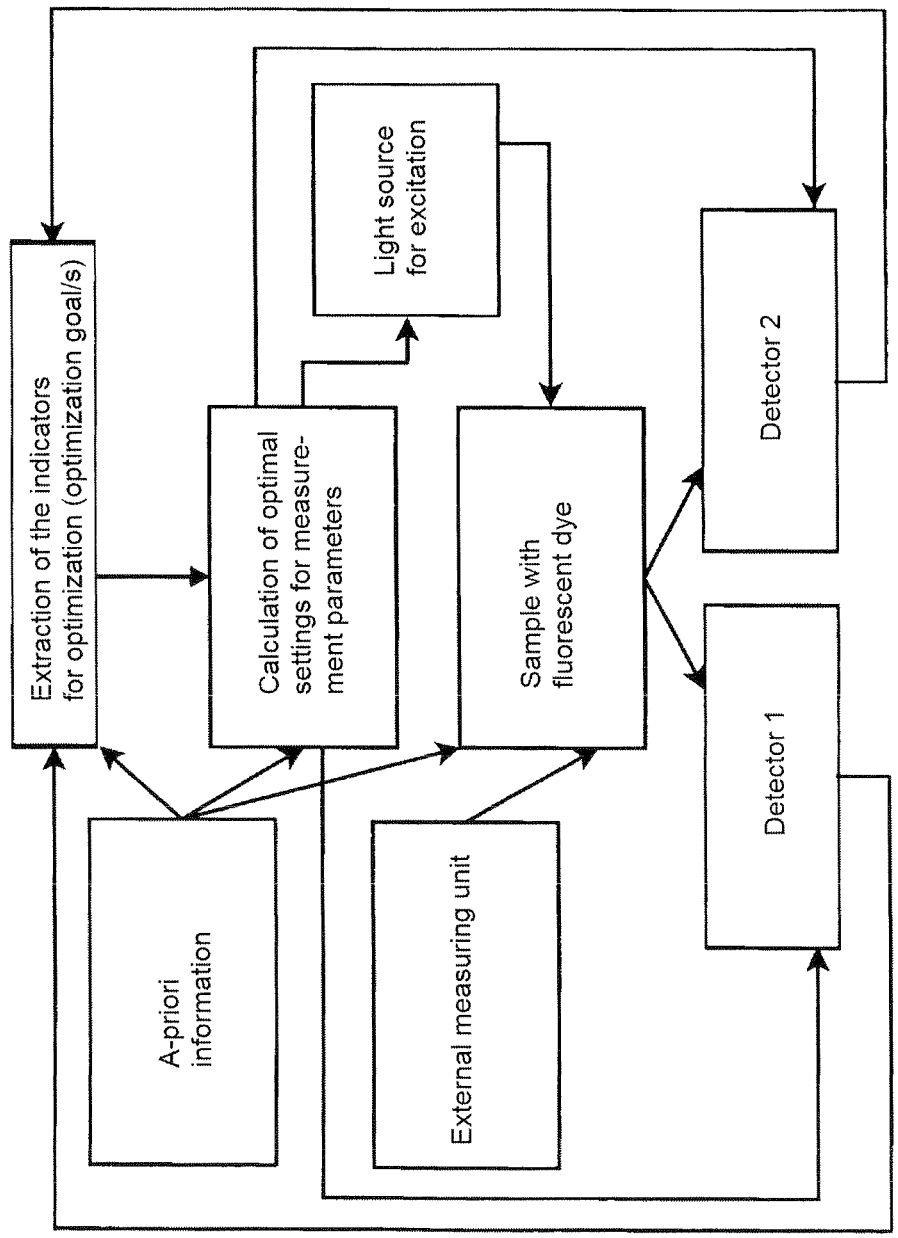
FIG. 5 shows a pseudo-flowchart of an optimization process serving as an example.

Owing to the fact that the increase in the fluorescence yield and the reduction in bleaching are highly dependent upon the dye and sample in high-resolution fluorescence microscopy using SIM or SPEM, a feedback-controlled optimization of the fluorescence yield is carried out by varying the pulse sequence (pulse duration and/or pulse repetition rate) at a constant mean output (accordingly, a signal increase can only occur through reduced bleaching). FIG. 4 shows the feedback from the detected fluorescence signal for readjusting the light source LQ, the structuring unit 7, and the filter. FIG. 5 shows, by way of example, an optimization for a microscope measurement with two detectors, an external measuring unit, and an excitation light source taking into account information known a priori (e.g., about the fluorescent dye, in the form of a pseudo-flowchart).

Figure 6:
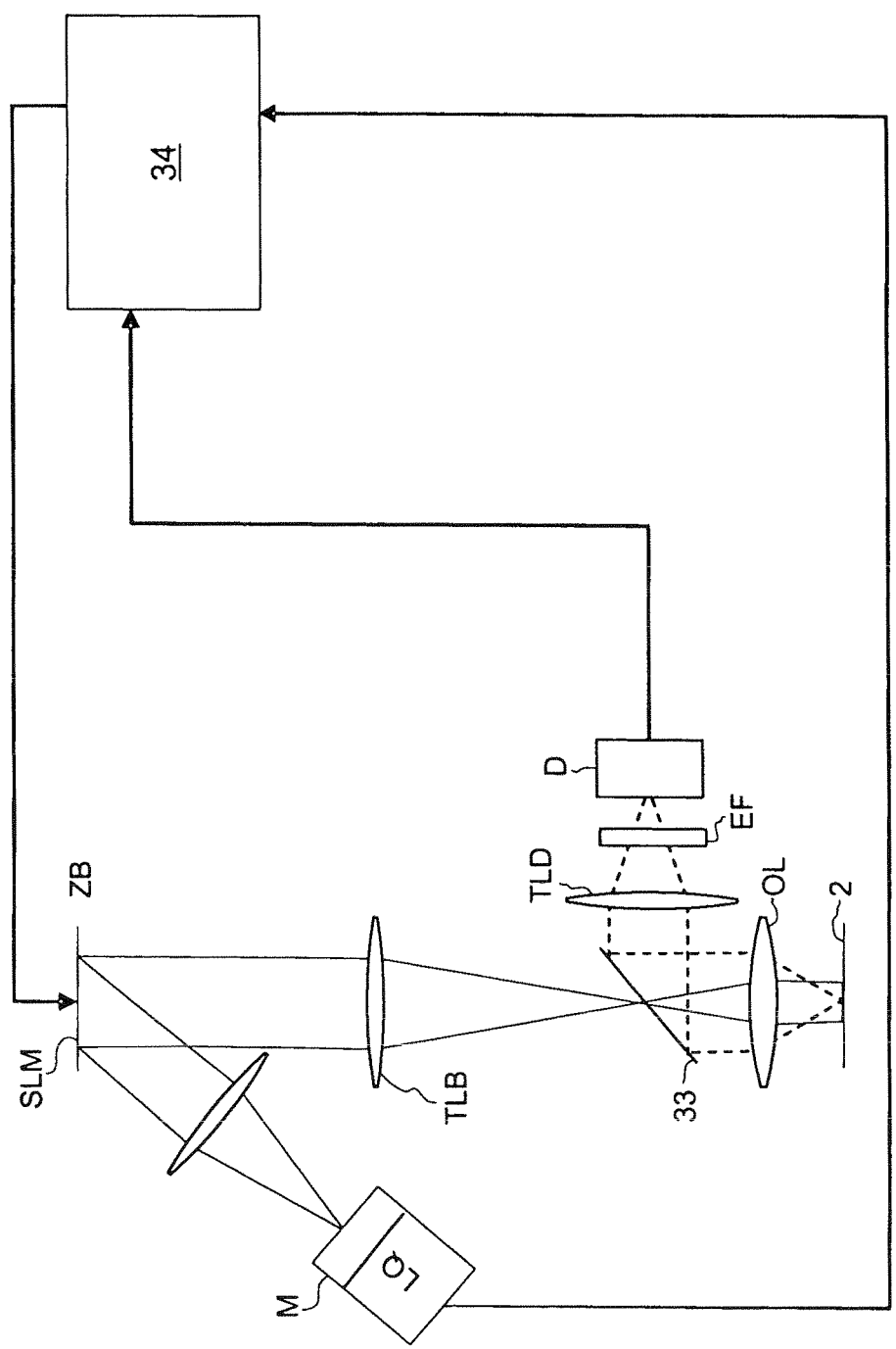
FIG. 6 shows a schematic view of another widefield microscope with temporally and spatially modulated excitation and feedback for optimization.

A sample-dependent optimization of the image quality is also possible based on other illumination parameters or image recording parameters. One possibility consists in the optimization of excitation through evaluation of the fluorescence signal until a predetermined signal-to-noise ratio is achieved. In so doing, it is particularly advantageous that the excitation time or excitation intensity is varied locally in the form of the pulse sequence by means of an imaging unit (DMD, LCD modulator, LCOS modulator—which can advantageously be used at the same time for structuring) while evaluating the camera image which is inputted at a high frame rate, which is shown schematically in FIG. 6. An average is taken of all of the individual images recorded in this way for a position and orientation of the structuring. However, it is also possible and especially simple in terms of technology to vary the excitation time or excitation intensity globally with respect to the entire image at a respective position of the structuring module by means of direction modulation of the laser accompanied by evaluation in the manner described above, or with evaluation of an averaged signal of a point detector which is calibrated with the camera and which detects a fraction of the fluorescent light which is coupled out through a beamsplitter. In both cases, an intensity correction is carried out prior to the reconstruction of the result image by calculating the structured images relative to one another based on the known local or global variation of the excitation time or excitation intensity.

In so doing, there is a dynamic expansion and at the same time, taking into account the dynamics of the visualization medium, the possibility of using this information for an optimal display of the image data. In this optimization, a structured line illumination with confocal detection is preferred for discrimination of out-of-focus light (which can dominate the detected fluorescence signal in some cases).

Based on user choice, the exposure time and/or the excitation pulse sequence are changed by the control software executed by the control unit 34 in such a way that the full dynamic range of the camera is utilized in every individual image. In so doing, the weighting between camera gain, pulse sequence and exposure time can be carried out by means of a-priori information about the bleaching rate of the dye or, for example, by measuring this bleaching rate at locations in the sample which were marked by the user as having no interest for the image recording (for example, a neighboring cell). In addition, within the available recording time, the dynamic range of the recording can be expanded beyond the dynamic range of the camera by recording all of the individual images of the structured illumination image stack with a plurality of exposure parameters (integration time, pulse sequence, and camera gain) and calculating these images to form an image stack with an expanded dynamic range. In particular, the dynamic range can be expanded not only globally in the image by adapting the pulse sequence, but can also be optimally expanded only locally. In structured line illumination, this is preferably effected by adjusting the line intensity so that the camera is driven in every line and recording the line intensity used per line.

Another arrangement for local optimization of the illumination parameters and recording parameters and for expanding dynamics is shown schematically in FIG. 7. It contains a SLM, for example, a DMD, in an intermediate image ZB which locally readjusts the structured illumination in order to achieve maximum dynamic range of the recording. In this case, the structuring can be generated by a structuring module SM_P in the pupil plane which provides the Fourier transform of the desired structured illumination in the sample 2. An embodiment of the structuring module SM_P with light-conducting fibers is shown in FIG. 7B and is described in DE 10 2007 047 466 A1. The relevant information for the expansion of dynamics is contained in the local laser intensity that is used and in the detected fluorescence. An image stack for the structured illumination algorithm with expanded dynamic range can now be calculated from this information and the calculation artifacts can be reduced, since the artifact amplitude depends substantially on the SNR in the individual images.

Since the nonlinearity in SPEM depends not only on the environmental conditions but also on the illumination conditions, namely, particularly the excitation intensity and the intensity of the activation laser, the latter are preferably also adapted spatially (or temporally for different individual images) in such a way that optimal nonlinearity is achieved at all times and at all locations. A possible construction for this purpose uses a SLM in the intermediate image plane in order to achieve this local adaptation.

The modulation frequency (i.e., the spatial frequency) of the illumination structure can be optimized according to the invention. For example, the highest possible modulation frequency can be selected so that a sufficient ratio of the modulation amplitude to background is still achieved. This evaluation can be carried out in the spatial domain or in the spatial frequency domain. In particular, the modulation frequency can be changed as a function of the depth of penetration into the sample in order to counter the decrease in modulation contrast at increasing depth in samples with a refractive index mismatch by reduced modulation frequency.

Alternatively, the modulation frequency of the illumination structure can be selected low enough that at least a multiple of this frequency is still transmitted by the objective. The illumination parameters and recording parameters such as pulse sequence, exposure time, and camera gain are varied until the amplitude of the multiples of the modulation frequency are at a maximum with minimal bleaching of the sample. With these illumination parameters and recording parameters and a structure modulation frequency just below the limiting frequency of the microscope objective, a complete image stack is recorded for SPEM and a result image with enhanced resolution is reconstructed from the latter.

Aside from the modulation amplitude which can be obtained from an individual image, the artifact amplitude can also be taken as feedback parameter for the selection of modulation frequency. The artifact amplitude is calculated from a complete SIM image stack and the calculation algorithm and is minimized by reducing the modulation frequency until it lies below the typical visual threshold. The artifact amplitude is calculated from the residual modulation amplitudes by incomplete separation of different orders and drops in the frequency spectrum due to insufficient modulation contrast. It is a quantitative measure for the artifacts in the reconstructed result image.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

REFERENCE NUMERALS 2 sample
3 sample holder
5 microscope objective
7 structuring module
9 pupil
17 actuator
19 imaging unit
20 collimating optics
21 microscope objective
22 sample
23 laser
24 laser flap
25 attenuator
26 fiber coupler
27 tube lens
28 filter
29 dichroic beamsplitter
30 scanner mirror
31 pinhole diaphragm
32 detector array 33 main beamsplitter
34 control unit
D detection module
MI microscope
L illumination module
S scanning module
LQ light source
OL microscope objective
G grating
M modulator
TLB tube lens illumination
TLD tube lens detection
ZB intermediate image plane
EF emission filter
DMD digital micro-mirror array
SLM spatial light modulator
SM_P fiber-based structuring module in the pupil plane

The invention claimed is:

1. A method for high-resolution imaging of a sample labeled with a fluorescent dye by means of a microscope, the method comprising:
    illuminating the sample sequentially in a plurality of phases by structured, pulsed excitation light; and
    recording fluorescent light emitted by the sample for each phase in a respective structured individual image;
    reconstructing a result image of the sample with enhanced resolution from the individual images;
    wherein an optimal adjustment is determined for at least one parameter of the illumination and/or at least one parameter of the recording, and
    wherein a pulse sequence of the illumination is varied pixel by pixel based on intermediate images of the fluorescent light recorded with a higher frame rate than the individual images, and the result image is reconstructed after intensity correction of the individual images is carried out based on the variation of the pulse sequence.

2. The method according to claim 1;
    wherein the optimal adjustment of the parameter is determined by:
        a feedback based on the individual images, based on additional intermediate images, or based on a signal of a point detector to which a fraction of the fluorescent light is coupled out; and
        varying the parameter.

3. The method according to claim 2;
    wherein the variation of the parameter is carried out at a substantially constant average power of the excitation light.

4. The method according to claim 1;
    wherein a simulation of illumination and recording is carried out to determine the optimal adjustment of the parameter.

5. The method according to claim 1;
    wherein an adjustment is determined as optimal when a maximum signal-to-noise ratio or at least a predetermined signal-to-noise ratio results in an intermediate image, in an individual image, or in the result image by this adjustment.

6. The method according to claim 5;
    wherein a predetermined weighting of additional optimization goals is taken into account in addition to a weighting for the signal-to-noise ratio when determining the optimal adjustment.

7. The method according to claim 1;
    wherein the structuring of the excitation light is generated by means of the same imaging unit.

8. The method according to claim 1;
    wherein a measurement abort criterion is checked during the recording, and the recording is terminated, or at least simplified, when the measurement abort criterion is met.

9. The method according to claim 8;
    wherein, as a measurement abort criterion, a check is made as to whether a modulation contrast falls below a predetermined contrast threshold or whether a movement distance of the sample exceeds a movement threshold.

10. The method according to claim 1;
    wherein a test preparation in the form of a homogeneous multi-colored dye film having a thickness of less than 100 nm and with no refractive index mismatch with the immersion liquid of the objective of the microscope or in the form of a test sample with multi-colored beads between 200 nm and 500 nm in size is used to determine an optimal adjustment of a parameter.

11. A non-transitory computer readable media storing a program of operating a microscope to achieve high-resolution imaging of a sample labeled with a fluorescent dye;
    wherein the computer program is performed by a computer system that comprises one or more processors, a memory operatively coupled to at least one of the processors, and a computer-readable storage medium encoded with instructions by at least one of the processors and operatively coupled to at least one of the processors, the computer program comprising instructions of:
        implementing the method of claim 1.

12. A control configured to implement the method of claim 1.

13. A microscope comprising:
    unit according to claim 12.

14. The method according to claim 1;
    wherein an optimal adjustment is determined for at least one of "wavelength of the illumination", "pulse sequence of the illumination", "wavelength range of the recording", "exposure time of the recording", and "gain of the recording".

* * * * *